US011651847B2

(12) United States Patent
Long et al.

(10) Patent No.: US 11,651,847 B2
(45) Date of Patent: May 16, 2023

(54) DOSE VOLUME HISTOGRAM AND DOSE DISTRIBUTION BASED AUTOPLANNING

(71) Applicant: The Board of Regents of The University of Texas System, Austin, TX (US)

(72) Inventors: Troy Long, Fort Worth, TX (US); Mingli Chen, Coppell, TX (US); Steve Jiang, Southlake, TX (US); Weiguo Lu, Coppell, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 734 days.

(21) Appl. No.: 16/558,698

(22) Filed: Sep. 3, 2019

(65) Prior Publication Data

US 2020/0075151 A1 Mar. 5, 2020

Related U.S. Application Data (60) Provisional application No. 62/725,625, filed on Aug. 31, 2018.

(51) Int. Cl.
*A61N 5/10* (2006.01)
*G16H 20/40* (2018.01)

(52) U.S. Cl.
CPC .......... *G16H 20/40* (2018.01); *A61N 5/1031* (2013.01)

(58) Field of Classification Search
CPC ... A61N 5/1031; A61N 5/1047; A61N 5/1082
See application file for complete search history.

(56) References Cited

U.S. PATENT DOCUMENTS

| 5,602,892 A | 2/1997 | Llacer |
| 6,411,675 B1 * | 6/2002 | Llacer ................... G16H 50/50 378/65 |
| 2013/0197878 A1 | 8/2013 | Fiege et al. |

FOREIGN PATENT DOCUMENTS

WO 2017/156316 9/2017

OTHER PUBLICATIONS

PCT International Application No. PCT/US2019/49306, The International Search Report and the Written Opinion of the International Searching Authority, dated Nov. 27, 2019, 8 pages.
Long et al., "Threshold-Driven Optimization for Reference-Based Auto-Planning", Physics in Medicine and Biology, IOP Publishing, Feb. 8, 2018, 8 pages.

(Continued)

*Primary Examiner* — Christine H Matthews
(74) *Attorney, Agent, or Firm* — DLA Piper LLP (US)

(57) ABSTRACT

A method and system for generating a voxel-based quadratic penalty model for automatic intensity modulated radiation therapy (IMRT) treatment planning are disclosed herein. A computing system generates an initial assignment of threshold values to a penalty function for IMRT treatment planning. The computing system receives an update to a dose value associated with the IMRT treatment planning. The computing system dynamically updates the threshold values based on the updated dose value. The computing system continues to iterate the threshold values based on further updated dose values.

20 Claims, 7 Drawing Sheets

(56) References Cited

OTHER PUBLICATIONS

Appenzoller, et al., "Predicting dose-volume histograms for organs-at-risk in IMRT planning", International Journal of Radiation Oncology Biology Physics, vol. 39, Dec. 2012, 2 pages.
Boyd, et al., "Convex optimization", Cambridge university press, Mar. 15, 1999, 216 pages.
Breedveld, et al., "Fast, multiple optimizations of quadratic dose objective functions in IMRT", Physics in Medicine & Biology, vol. 51.14, 2006, pp. 3569-3579.
Craft, et al., "Shared data for intensity modulated radiation therapy (IMRT) optimization research: the CORT dataset", GigaScience, vol. 3:37, 2014, 12 pages.
Dobler, et al., "Comparison of direct machine parameter optimization versus fluence optimization with sequential sequencing in IMRT of hypopharyngeal carcinoma", Radiation Oncology, vol. 2:33, Sep. 6, 2007, 7 pages.
Hardemark, et al., "Direct machine parameter optimization", Pinnacle RaySearch White Paper, Philips, 2003, 8 pages.
Li, et al., "Highly efficient training, refinement, and validation of a knowledge-based planning quality-control system for radiation therapy clinical trials", International Journal of Radiation Oncology Biology Physics, vol. 97.1, Jan. 1, 2017, pp. 164-172.
Long, et al., "Continuous leaf optimization for IMRT leaf sequencing", Medical physics, vol. 43.10, Sep. 13, 2016, pp. 5403-5411.
McIntosh, et al., "Voxel-based dose prediction with multi-patient atlas selection for automated radiotherapy treatment planning", arXiv preprint arXiv:1608.04330, Phys. Med. Biol., Aug. 15, 2016, 18 pages.
Men, et al., "GPU-based ultrafast IMRT plan optimization", Physics in Medicine & Biology, vol. 54.21, Oct. 14, 2009, 10 pages.
Shiraishi, et al., "Knowledge-based prediction of three-dimensional dose distributions for external beam radiotherapy", Medical physics, vol. 43.1, Dec. 6, 2015, pp. 378-387.
Wu, et al., "Data-driven approach to generating achievable dose-volume histogram objectives in intensity-modulated radiotherapy planning", International Journal of Radiation Oncology Biology Physics, vol. 79, 2010, 7 pages.
Wu, et al., "Treatment plan modification using voxel-based weighting factors/dose prescription", Physics in Medicine & Biology, vol. 48.15, Jul. 22, 2003, pp. 2479-2491.
Zarepisheh, et al., "A DVH-guided IMRT optimization algorithm for automatic treatment planning and adaptive radiotherapy replanning", Medical physics, vol. 41.6 Part1, 2014, 14 pages.
Zhu, et al., "A planning quality evaluation tool for prostate adaptive IMRT based on machine learning", Medical physics, vol. 38.2, Jan. 11, 2011, pp. 719-726.

\* cited by examiner

DOSE VOLUME HISTOGRAM AND DOSE DISTRIBUTION BASED AUTOPLANNING

CROSS-REFERENCE TO RELATED APPLICATION

This application claims priority to U.S. Provisional Application No. 62/725,625, filed Aug. 31, 2018, which is hereby incorporated by reference in its entirety.

BACKGROUND

Conventional treatment planning for Intensity Modulated Radiation Therapy (IMRT) involves solving a so-called fluence map optimization (FMO) problem where non-homogeneous intensity profiles are found that produce a desirable dose distribution in the patient, with high dose to the planning target volume (PTV) and low dose to the organs-at-risk (OARs). These intensity profiles are then sequenced into apertures to produce a deliverable treatment plan. In FMO, a voxel-based quadratic penalty is often employed to quantify the quality of the dose distribution (e.g. Wu et al (2003), Breedveld et al (2006), Men et al (2009), Zarepisheh et al (2014)). For some set of voxels, V, let $d_i$ be the dose to voxel $i \in V$. Equation (1) shows a general form of the conventional voxel-based quadratic penalty function:

$$F(d_i, T_i^o, T_i^u, \alpha_i^o, \alpha_i^u) = \qquad (1)$$

$$\begin{cases} \frac{\alpha^o}{|V^{s(i)}|}(d_i - T_i^o)_+^2 & \text{for } i \in V^{OAR} \\ \frac{\alpha^o}{|V^{s(i)}|}(d_i - T_i^o)_+^2 + \frac{\alpha^u}{||V^{s(i)}|}+(T_i^u - d_i)_+^2 & \text{for } i \in V^{PTV} \end{cases},$$

where $T_i^o$ and $T_i^u$ are the overdosing and underdosing thresholds, respectively, $\alpha_i^o$ and $\alpha_i^u$ are the overdosing and underdosing penalty weights, and $V^{s(i)}$ is the set of voxels in the structure of which i is a member. A piecewise quadratic objective has several major benefits. First, it is a convex function, and there exist efficient optimization algorithms for convex problems (Boyd and Vandenberghe 2004). Second, this objective can reproduce any feasible dose distribution generated from IMRT fluence map optimization, $d^*$, by setting $T_i^o = T_i^u = d_i^*$. Third, treatment plans generated with a voxel-based quadratic objective perform well when evaluated with dose volume histogram (DVH) objectives (Wu et al 2003, Breedveld et al 2006, Zarepisheh et al 2014).

Conventionally, threshold values are set to single values at the structure level, as seen in equation (2), with $P_i$ as the prescription dose for voxel i. The $P_i$ dose value is often increased slightly to ease the objective weight tuning for finding a plan that meets PTV underdosing requirements.

$$T_i^o = T_i^u = P_i = \begin{cases} 0 & \text{for } i \in V^{OAR} \\ P_i & \text{for } i \in V^{PTV} \end{cases} \qquad (2)$$

While attempting to achieve an 'ideal' plan of perfectly conformal PTV dose and 0 dose to OARs may make intuitive sense in theory, practically planning with idealized threshold values generates some problems. These threshold values are not realistically achievable, and the burden of plan manipulation falls upon the penalty weight vectors, $\alpha^u$ and $\alpha^o$. $\alpha$-values are patient specific and unknown a priori, which leads to a potentially time-consuming process of weight tweaking to achieve a desirable plan. These weights are not easily interpretable, and are often selected to be many orders of magnitude apart due to large deviation of the threshold from realistic dose. Ideal PTV deviation will be much smaller than OAR deviation, and that discrepancy causes for unintuitive guess-and-check techniques to be used when planning. Zarepisheh et al. (2014) investigated a framework for automatically updating the weights on the voxel-level, but experienced some problems with consistency in quality and lack of control on plan trade-offs.

SUMMARY

In some embodiments, a method for generating a voxel-based quadratic penalty model for automatic intensity modulated radiation therapy (IMRT) treatment planning is disclosed herein. A computing system generates an initial assignment of threshold values to a penalty function for IMRT treatment planning. The computing system receives an update to a dose value associated with the IMRT treatment planning. The computing system dynamically updates the threshold values based on the updated dose value. The computing system continues to iterate the threshold values based on further updated dose values.

In some embodiments, a system for generating a voxel-based quadratic penalty model for automatic intensity modulated radiation therapy (IMRT) treatment planning is disclosed herein. The system includes a processor and a memory. The memory has programming instructions stored thereon, which, when executed by the processor, performs one or more operations. The one or more operations include generating an initial assignment of threshold values to a penalty function for IMRT treatment planning. The one or more operations further include receiving an update to a dose value associated with the IMRT treatment planning. The one or more operations further include dynamically updating the threshold values based on the updated dose value. The one or more operations further include continuing to iterate the threshold values based on further updated dose values.

In some embodiments, a non-transitory computer readable medium is disclosed herein. The non-transitory computer readable medium has instructions stored thereon, which, when executed by a processor, cause the processor to perform an operation. The operation includes generating, by a computing system, an initial assignment of threshold values to a penalty function for IMRT treatment planning. The operation includes receiving, by the computing system, an update to a dose value associated with the IMRT treatment planning. The operation includes dynamically updating, by the computing system, the threshold values based on the updated dose value. The operation includes continuing, by the computing system, to iterate the threshold values based on further updated dose values.

BRIEF DESCRIPTION OF THE DRAWINGS

Various objectives, features, and advantages of the disclosed subject matter can be more fully appreciated with reference to the following detailed description of the disclosed subject matter when considered in connection with the following drawings, in which like reference numerals identify like elements.

FIG. 5A is a block diagram illustrating a computing device, according to example embodiments.

FIG. 5B is a block diagram illustrating a computing device, according to example embodiments.

The drawings are not necessarily to scale, or inclusive of all elements of a system, emphasis instead generally being placed upon illustrating the concepts, structures, and techniques sought to be protected herein.

DETAILED DESCRIPTION

One or more techniques described herein implement threshold values as the driving force in the voxel-based quadratic penalty model for automatic IMRT treatment planning. The computing system iteratively updates the threshold values, not the weights, so that the threshold values match the iteratively updated dose values. That is, such re-ordering of threshold values provides consistent distributions between the updated dose and the distribution generated from the reference DVH and spatial assignment. By having consistent, realistic deviations, the computing system can better control the dose distribution within beamlet intensity space.

2.1 Threshold-Driven Optimization Motivation

Consider the conventional fluence map optimization problem with voxel-based quadratic penalties:

$$(P^{FMO}) \quad \underset{x,d}{\text{minimize}} \sum_{i \in V} F(d_i, T_i^o, T_i^u, \alpha_i^o, \alpha_i^u) \quad (3)$$

$$\text{subject to } d_i = \sum_{j \in N} D_{ij} x_j \quad \forall \ i \in V \quad (4)$$

$$x_j \geq 0 \ \forall \ j \in N, \quad (5)$$

where N is the set of beamlets and $D_{ij}$ is the dose from beamlet j to voxel i at unit intensity. If an ideal dose distribution d* is FMO-deliverable (i.e. there exists x*≥0 such that d*=Dx*), setting $T_i^o=T_i^u=d_i^*$ and $\alpha_i^o=\alpha_i^u>0$ will allow for $P^{FMO}$ to find a fluence map that achieves this ideal dose. However, d* is not explicitly known a priori.

While there have been recent advances in dose prediction algorithms (Shiraishi and Moore 2016, McIntosh and Purdie 2017) predicting the actual dose distribution is difficult. Generating a realistic, clinically desirable DVH is less difficult (Zhu et al 2011, Appenzoller et al 2012, Li et al 2017). Given some DVH, the computing system can assign dose to voxels based on some spatial assignment of the DVH dose values. This spatial assignment can be simple, such as sorted voxel distance to the PTV (Appenzoller et al 2012), or more sophisticated using machine learning or analytics techniques. Even the most sophisticated dose prediction and spatial assignment algorithms may not produce the overall ideal dose distribution, or even a feasible one for the patient (Wu et al 2011). However, the spatial assignment is improved (see section 2.3), a threshold-driven objective can be effective in shaping dose to a clinically desirable treatment.

2.2. Threshold-Driven FMO Objective

A threshold-driven penalty function must be able to adequately perform when the reference DVH is easy-to-achieve or infeasible. Thus two quadratic penalties are applied to each voxel to handle both of these situations.

TABLE 1

Current dose, $d^s$, with associated voxel index.

| Voxel index | $d^s$ |
|---|---|
| 1 | 2.2 |
| 2 | 3.5 |
| 3 | 1.6 |

TABLE 2

Example reordering of $h^s$ and assignment to voxel index.

| $h^s$ | $h^s[d^s]$ | $h^s \rightarrow$ Voxel index |
|---|---|---|
| 1.7 | 2.3 | 1.7 → 3 |
| 2.3 | 3.9 | 2.3 → 1 |
| 3.9 | 1.7 | 3.9 → 2 |

The primary threshold-driven penalty pulls dose to reference values and the secondary penalty function pulls the dose toward ideal values.

Let F ($d_i$, $T_i^o$, $T_i^u$, $\alpha_i^o$, $\alpha_i^u$) be the primary penalty, where $\alpha_i^o$ and $\alpha_i^u$ are structure-level weights defining the relative importance of violating threshold dose values, $T_i^o$ and $T_i^u$, which are derived from the reference DVH. Recall that the initial assignment of threshold values follows some scheme, such as distance-to-tumor. The primary penalty pulls dose toward the reference DVH by penalizing dose deviations from threshold dose values. The secondary penalty, F($d_i$, $P_i$, $P_i$, $\gamma_i$, $\gamma_i$), where $\gamma_i$ is a small value relative to $\alpha_i^u$ and $\alpha_i^o$, continues to pull dose values toward ideal values (prescription dose), $P_i$, when the primary penalty is relatively small. In some examples, $\gamma_i$ is defined to be constant for each structure s and proportionate to the mean squared reference dose, h, deviation from the prescription dose, P, for that structure. With ε as some small value, define $\gamma_i$ for voxel i in structure s as the following:

$$\gamma_i = \frac{\epsilon}{\left(\frac{1}{|V^s|} \sum_{k \in V^s} |h_k - P_k|\right)^2}. \quad (6)$$

Figure 1:
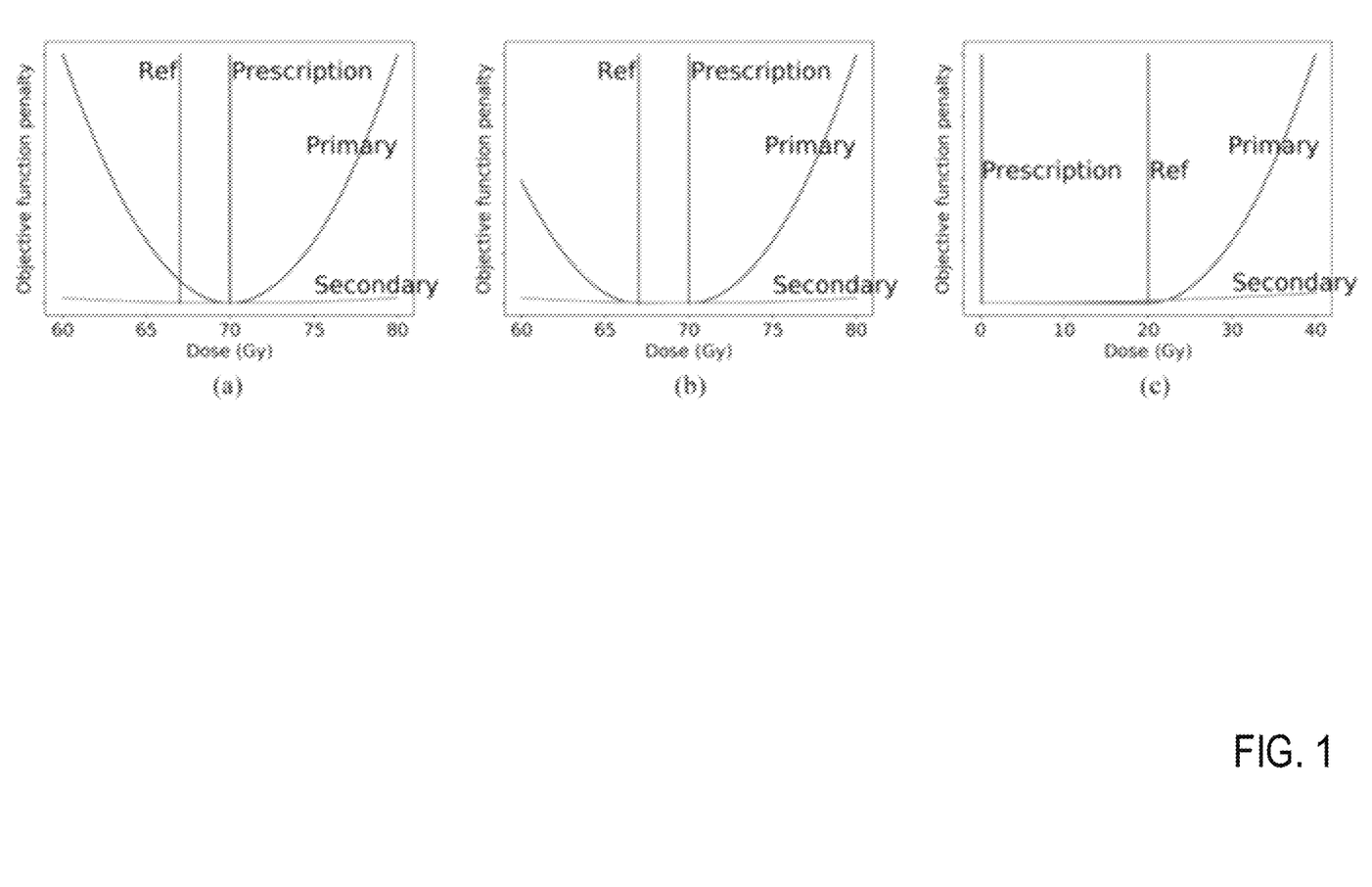
FIG. 1 is a block diagram of charts illustrating primary and secondary penalty functions for planning target volume and organs at risk, according to example embodiments.

The resulting threshold-driven FMO is presented in $P^{TFMO}$. As shown in FIG. 1, there is always a penalty applied for dose deviating from prescription values. When the dose deviates undesirably from reference values, the resulting primary penalty is much larger than the secondary.

$$(P^{TFMO}) \quad \underset{x,d}{\text{minimize}} \sum_{i \in V} [F(d_i, T_i^o, T_i^u, \alpha_i^o, \alpha_i^u) + F(d_i, P_i, P_i, \gamma_i, \gamma_i)] \quad (7)$$

$$\text{subject to } d_i = \sum_{j \in N} D_{ij} x_j \ \forall \ i \in V \quad (8)$$

$$x_j \geq 0 \ \forall \ j \in N \quad (9)$$

2.3. Spatial Update

Having a method for spatial assignment improvement is helpful because the initial guess may not be ideal, or even realistic, for a desired DVH. By iteratively improving the initial guess, the computing system can approach a realistic, feasible spatial assignment. Let $h^s$ be a vector of DVH dose values of length $|V^s|$ for structure s evenly sampled across fractional volume, assuming, for example, that all voxels in a structure have the same volume. These are the values the computing system may assign to voxels. Let $h^s[d^s]$ denote the reordering of $h^s$ to match the value orders of $d^s$. An example of this reordering can be found in tables 1 and 2, where the reference DVH values are reordered in voxel index space to match the ordering of the current dose, ds. Zarepisheh et al goes into mathematical detail for this voxel re-assignment. By such sorting, the computing system may find the closest spatial assignment to the current dose distribution (Zarepisheh et al 2014).

Given spatially assigned reference DVH h(d) and iteration t of n total threshold re-assignment iterations, calculate threshold values in the following way for voxel $i \in V^s$:

$$T_i^o = \begin{cases} h_i^s[d^s] & \text{for } i \in V^{OAR} \\ \max\left(P_i, \frac{t}{n} h_i^s[d^s] + \left(1 - \frac{t}{n}\right) P_i\right) & \text{for } i \in V^{PTV} \end{cases}, \quad (10)$$

$$T_i^u = \begin{cases} h_i^s[d^s] & \text{for } i \in V^{OAR} \\ \min\left(P_i, \frac{t}{n} h_i^s[d^s] + \left(1 - \frac{t}{n}\right) P_i\right) & \text{for } i \in V^{PTV} \end{cases}, \quad (11)$$

where t=0, . . . , n is the assignment index. In this formulation, the threshold is initially the preferred, idealized PTV coverage, and the threshold is relaxed to the reference DVH as the iteration progress. Because PTV coverage heavily motivates the final dose distribution, the prioritized PTV coverage in the spatial update promotes dose distributions that are guided to have 'superior' PTV coverage. As the PTV threshold values are relaxed $$\left(\frac{t}{n} \to 1\right)$$

to the reference DVH values from ideal ones, the spatial update will improve upon OAR assignment accuracy. First and last iteration of PTV penalties can be found in FIG. 1. For example, primary and secondary penalty functions for PTV (reference dose=67, prescription=70) and OAR (reference dose=20). The complete TORA framework is presented in algorithm 1. In the algorithm presented, d* refers to the optimal dose resulting from solving $P^{TFMO} \cdot \alpha_i^o$ and $\alpha_i^u$, when defined on the structure level, are used for determining the trade-offs between structures for deviating from $T_i^o$ and $T_i^u$. This can be used for navigating tradeoffs between structures or adding physician preference to the objective. For this, the computing system may set all $\alpha$-values the same value to illustrate the effectiveness of using threshold-values for shaping the dose distribution. $\alpha$-values can be useful in incorporating coverage/sparing preferences into the algorithm.

---

Algorithm 1. Threshold-driven optimization framework

Require: Reference DBH h, with initial spatial distribution h[d])
Require: $\alpha^o, \alpha^u, \gamma$
    function TORA (h,d,$\alpha^o,\alpha^u,\gamma$)
        for t = 0,...,n do
            Set $T_j^o, T_j^u$ according to equations (10) and (11)
            Solve $P^{TFMO}$ to get d*
            h = h[d*]
        end for
        return x*,d*
    end function

---

3. Results

The computing system may apply TORA to the CORT prostate and lung cases (Craft et al 2014). For each case, the computing system may generate reference DVHs through solving the conventional $P^{FMO}$ with objective function $\Sigma_{i \in V} F(d_i, P_i, P_i, \alpha_i^o, \alpha_i^u)$, where $\alpha$-values reflect relative importances between structures. These values were tuned to generate plans that prioritize PTV coverage or OAR sparing. The resulting DVHs were used as the reference DVH for the TORA framework. In some examples, $\alpha$-values used in TORA were fixed to 1 for the PTV and 1 for OARs, and $\varepsilon$ was set to 0.001 for all voxels. Other $\alpha$-values were tested, and the method is robust to non-extreme changes in these values. The impact and application of $\alpha$-value selection will be studied in a later manuscript. Beam orientations are consistent between reference and TORA plans. The initial spatial distribution, h(d), was found by sorting voxels by their Euclidean distance to the PTV surface. Ten iterations were used for the following results. For between five and fifteen iterations, the computing system performed well, with fewer being insufficient to adequately update the naive initial spatial assignment. Using more iterations saw little improvement in results with an increase in computation time. In Zarepisheh et al (2014), many more iterations were needed to converge on a meaningful result.

Figure 2A:
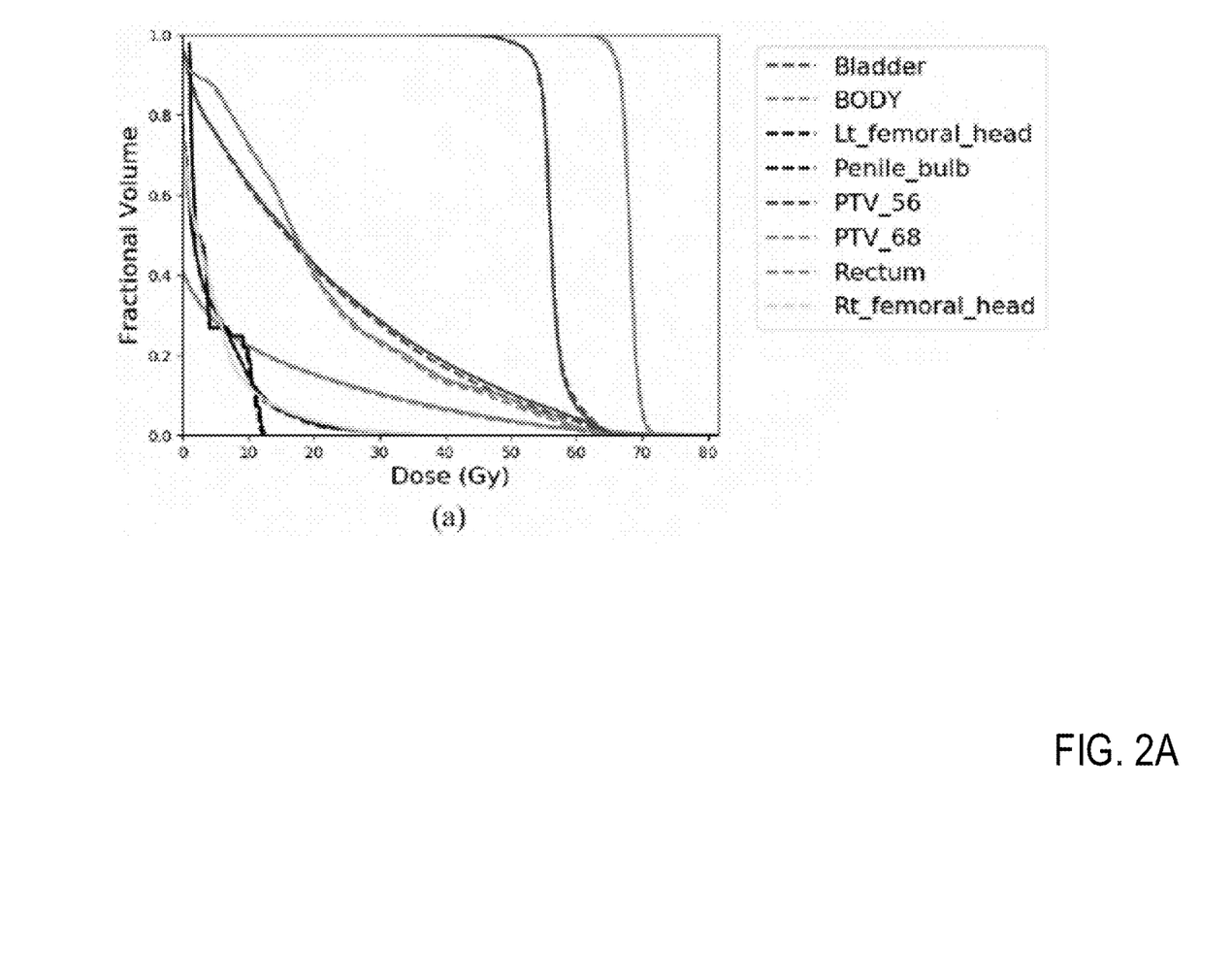
FIG. 2A is a dose volume histogram, according to example embodiments.
Figure 2B:
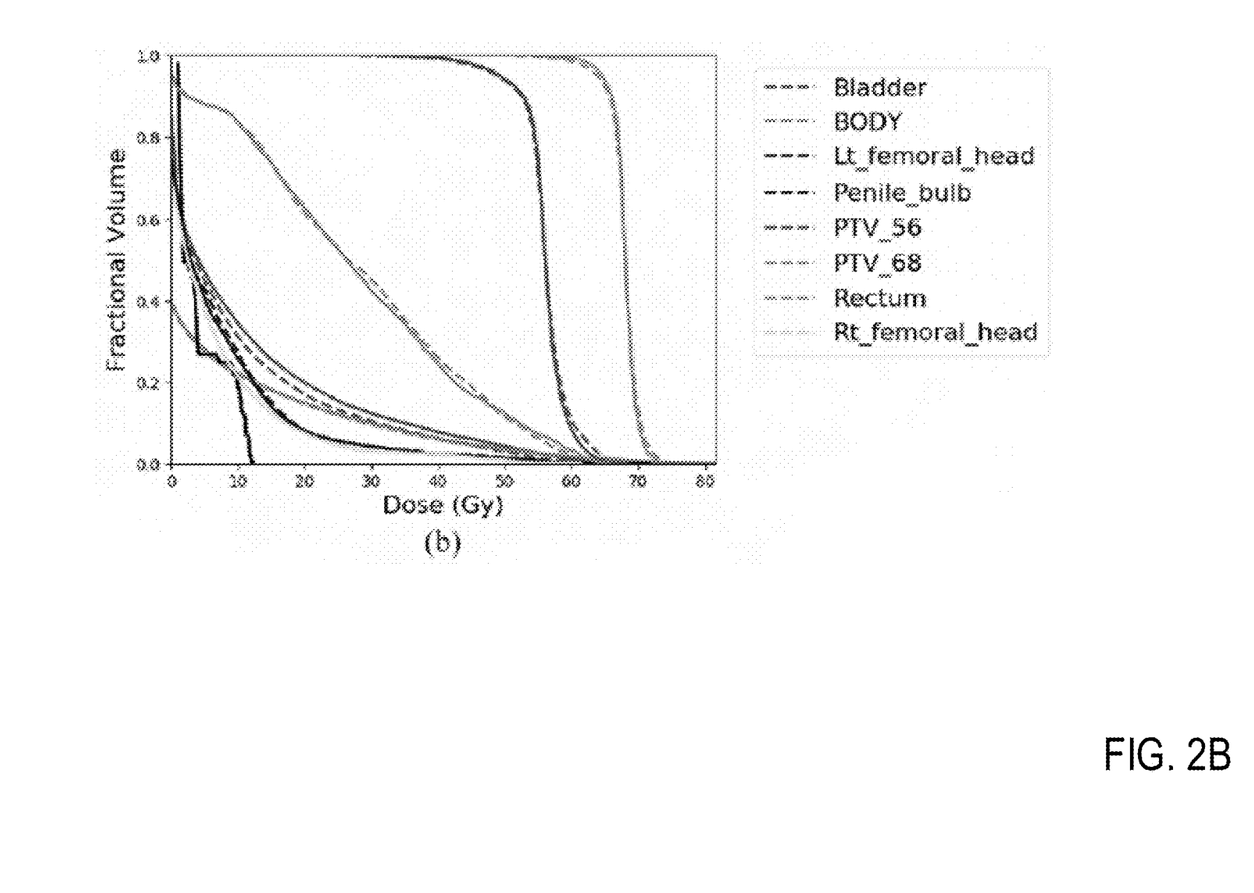
FIG. 2B is a dose volume histogram, according to example embodiments.
Figure 3A:
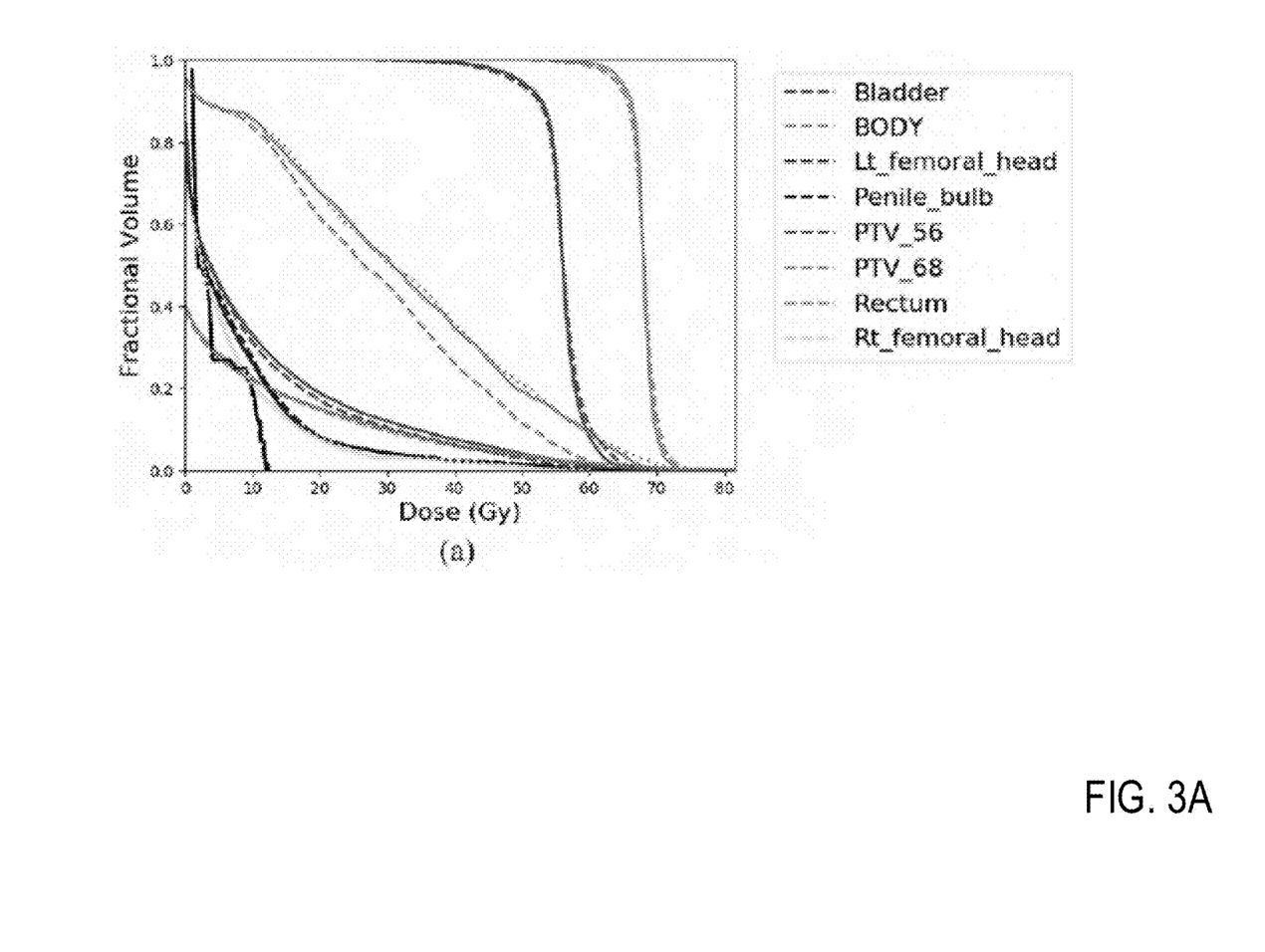
FIG. 3A is a block diagram of a prostate case, bladder sparing dose volume histogram, according to example embodiments.
Figure 3B:
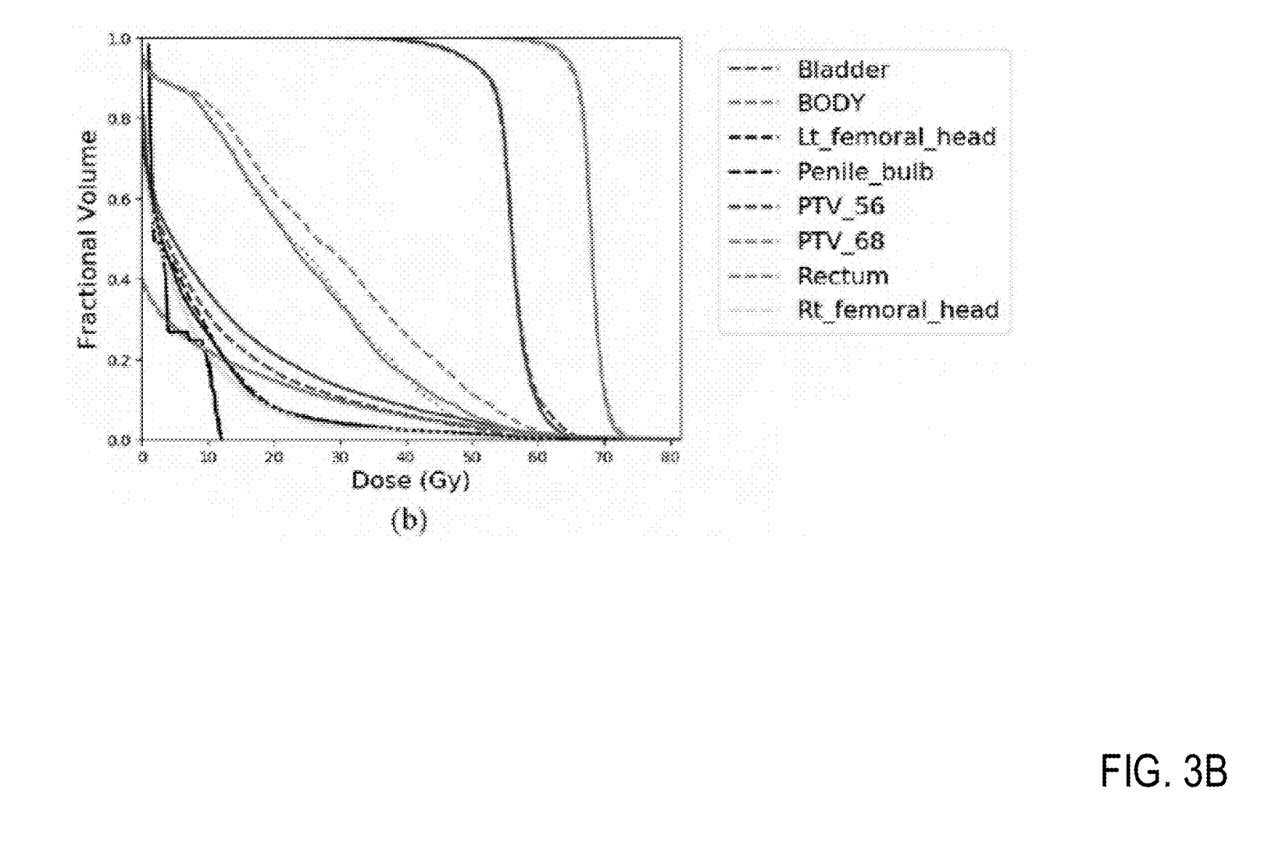
FIG. 3B is a block diagram of a reference dose volume histogram rectum decreased 15%, according to example embodiments.

The prostate cases used ten equi-spaced beams. Three reference plans were generated, one prioritizing bladder sparing, one prioritizing rectum sparing, and one evenly sparing the bladder and rectum. These reference DVHs were used to determine if this methodology can generate a plan with a DVH similar to that of a weight-tuned reference plan. In FIG. 2A, TORA's ability to generate plans that reproduce DVHs for the neutral and bladder sparing cases is shown. For example, in FIG. 2A, conventional quadratic-objective-optimized prostate case DVH are shown. Solid curves signify TORA DVH; dashed curves signify reference DVH. Similar results were found in the rectum sparing case. TORA generates DVHs very close to the reference DVHs. FIG. 2B illustrates a prostate case sparingly DVH. In FIG. 3A, the reference DVH from FIG. 2B was modified by scaling rectum dose up and down by 15%. In each case, plans with similar DVHs were generated. In FIG. 3A, where the reference DVH is easily achievable for this patient, TORA takes advantage of the relaxed rectum to improve PTV conformity. The infeasible reference DVH in FIG. 3B requires sacrificing dose quality across other OARs to achieve the new rectum DVH.

Figure 4A:
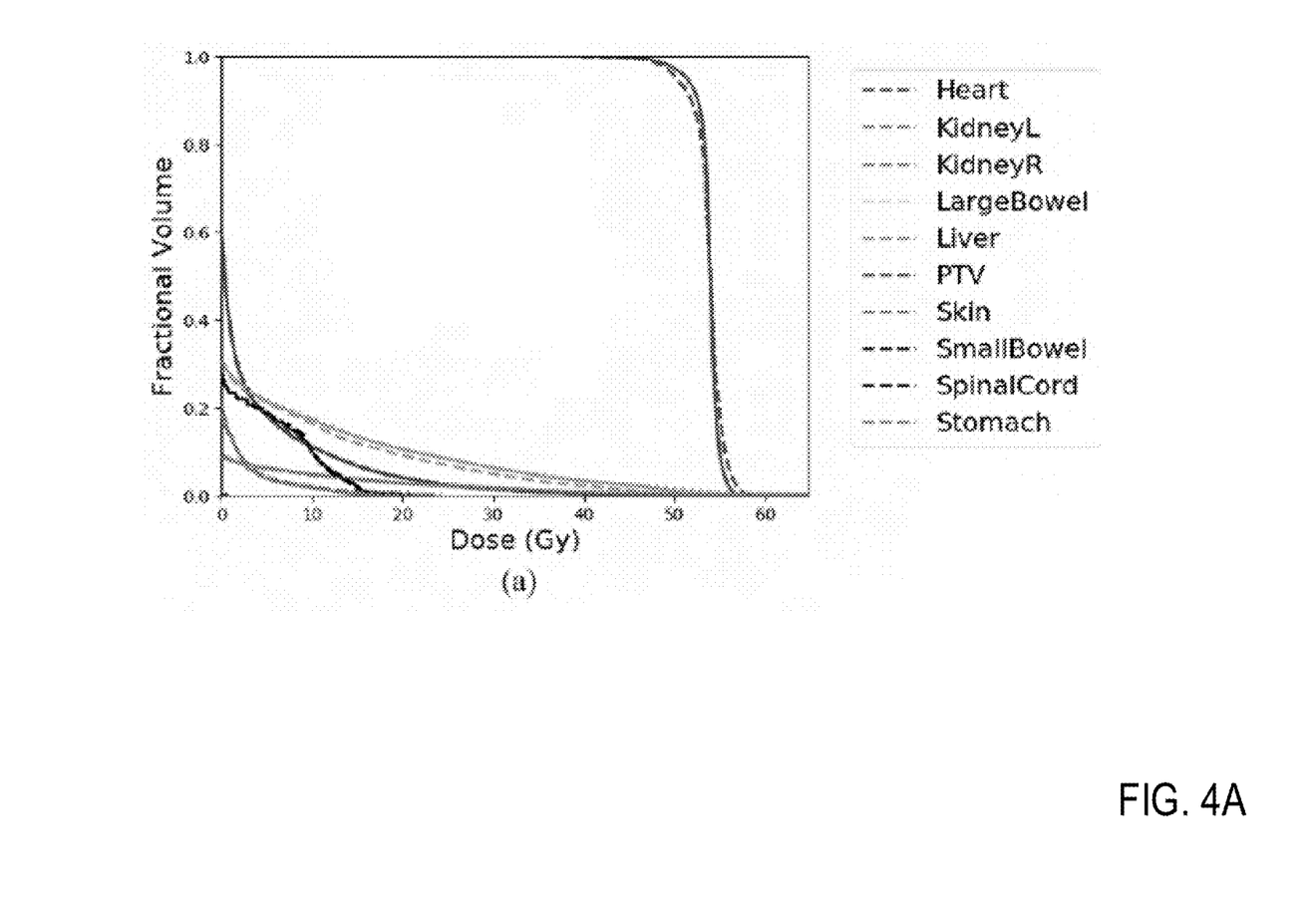
FIG. 4A is a block diagram illustrating liver case dose volume histogram, according to example embodiments.
Figure 4B:
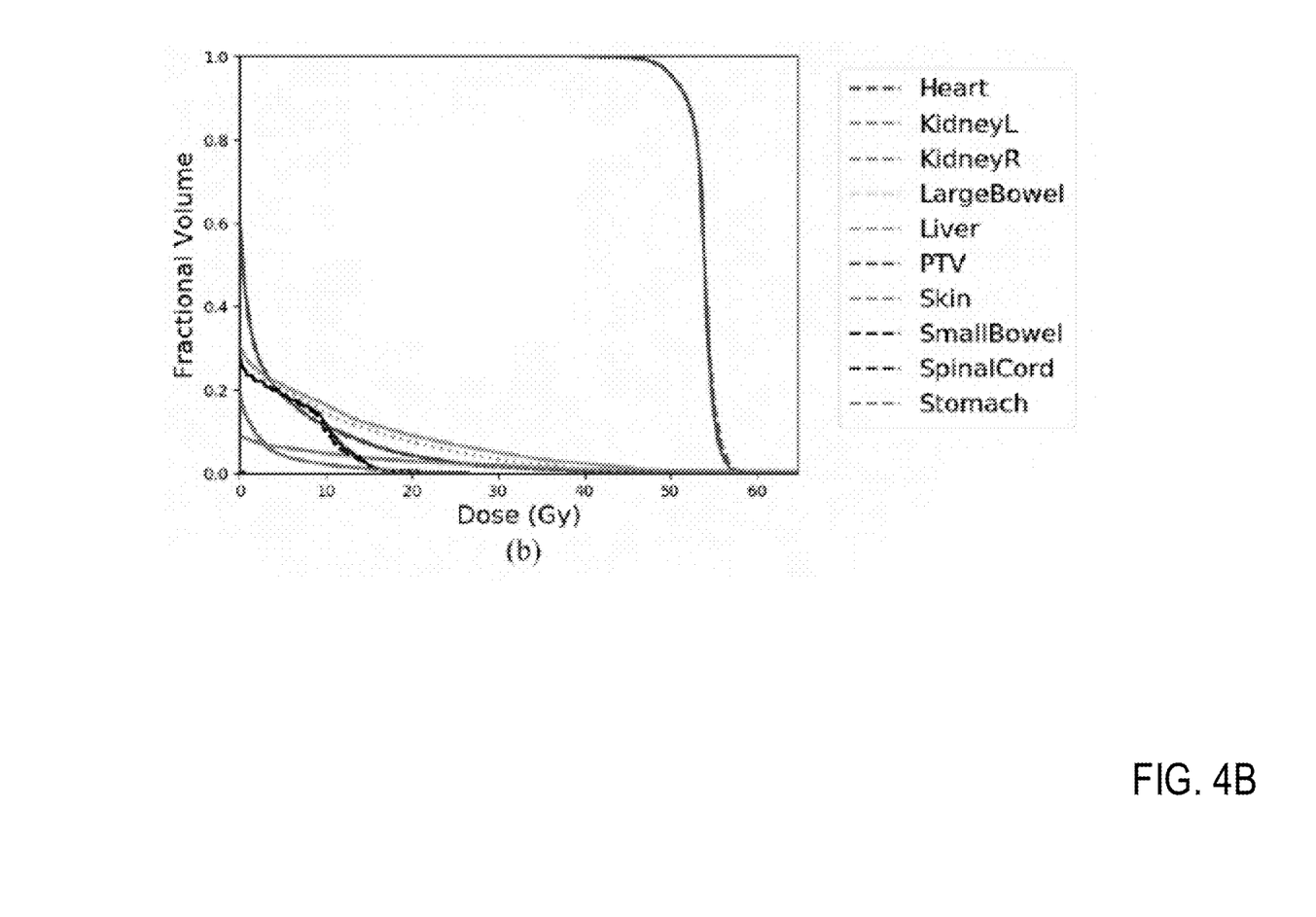
FIG. 4B is a block diagram illustrating reference DVH liver decreased 15%, according to example embodiments.

For the liver case, eight non-coplanar beams were used. TORA applied to the conventional quadratic-objective-optimized plan gave a nearly identical DVH and the DVH is omitted. The reference DVH was altered by increasing and decreasing liver dose by 15%. TORA took advantage of the sub-optimal DVH in FIG. 4A by improving PTV coverage. While TORA was unable to generate a plan to achieve the decreased liver dose as seen in FIG. 4B, other DVH goals were met.

4. Discussion and Conclusion

As an auto-planning methodology, TORA has several advantages. First, solving the convex subproblem, PTFMO, is relatively easy and can be implemented on GPU (Men et al 2009). For a clinical implementation of TORA, multiple plans can be generated off-line with little computational effort, as solving the full methodology can be done on the order of a few minutes on CPU, seconds on GPU. The intermediate DVH from PTFMO jumps around in early iterations, then settles in later iterations. Second, TORA can handle input DVHs that are sub-optimal or infeasible, making reasonable improvements and trade-offs, respectively, due to the relatively similar weighting factors. Lastly, $\alpha$- and $\gamma$-values can be used to influence how trade-offs are made. Patient sensitivity to these values may differ depending on patient geometry and reference DVH feasibility. However, in preliminary tests with additional cases, these values were fairly robust across patients. Distance-sorted voxels may be used to illustrate the effectiveness of the method even with an uninformed initial spatial distribution. A full reference dose distribution, instead of a DVH can be used as an input as well when deconstructed into the its DVH and spatial assignment.

This framework for automatic planning has some immediate application as well as potential to be extended to other applications and modalities. Currently, TORA can be used for IMRT (with leaf sequencing) and brachytherapy treatment planning models. Since all the methodology needs is a reference DVH and reasonable initial spatial assignment, TORA can also be used in pre-planning patient dose prediction as a guide for planners or adaptive planning. With some modification, TORA can be applied to VMAT. Finally, TORA can be extended for real-time interactive planning by directly manipulating machine parameters such as leaf position and aperture intensity (Hardemark et al 2003, Dobler et al 2007, Long et al 2016).

TORA provides a consistent, efficient, and intuitive framework for automatic treatment planning given a reference DVH. The work in Zarepisheh et al (2014) used reference DVHs to update the weights of quadratic penalty objectives, while the computing system described herein used them to update the threshold values. Automated weight updates may become very disproportionate and still lack proper driving force, which is a common shortcoming of weight tuning. In TORA, after obtaining optimal sub-problem dose, the threshold values are resorted to update the accuracy of the reference DVH spatial assignment. Such consistent numerical order may provide more effective and straightforward driving force. The methodology effectively handles both sub-optimal and infeasible DVHs.

FIG. 5A illustrates a system bus computing system architecture 500, according to example embodiments. System 500 may be representative of a computing system capable of performing the functions described above. One or more components of system 500 may be in electrical communication with each other using a bus 505. System 500 may include a processing unit (CPU or processor) 510 and a system bus 505 that couples various system components including the system memory 515, such as read only memory (ROM) 520 and random access memory (RAM) 525, to processor 510. System 500 may include a cache of high-speed memory connected directly with, in close proximity to, or integrated as part of processor 510. System 500 may copy data from memory 515 and/or storage device 530 to cache 512 for quick access by processor 510. In this way, cache 512 may provide a performance boost that avoids processor 510 delays while waiting for data. These and other modules may control or be configured to control processor 510 to perform various actions. Other system memory 515 may be available for use as well. Memory 515 may include multiple different types of memory with different performance characteristics. Processor 510 may include any general purpose processor and a hardware module or software module, such as service 1 532, service 2 534, and service 3 536 stored in storage device 530, configured to control processor 510 as well as a special-purpose processor where software instructions are incorporated into the actual processor design. Processor 510 may essentially be a completely self-contained computing system, containing multiple cores or processors, a bus, memory controller, cache, etc. A multi-core processor may be symmetric or asymmetric.

To enable user interaction with the computing device 500, an input device 545 may represent any number of input mechanisms, such as a microphone for speech, a touch-sensitive screen for gesture or graphical input, keyboard, mouse, motion input, speech and so forth. An output device 535 may also be one or more of a number of output mechanisms known to those of skill in the art. In some instances, multimodal systems may enable a user to provide multiple types of input to communicate with computing device 500. Communications interface 540 may generally govern and manage the user input and system output. There is no restriction on operating on any particular hardware arrangement and therefore the basic features here may easily be substituted for improved hardware or firmware arrangements as they are developed.

Storage device 530 may be a non-volatile memory and may be a hard disk or other types of computer readable media which may store data that are accessible by a computer, such as magnetic cassettes, flash memory cards, solid state memory devices, digital versatile disks, cartridges, random access memories (RAMs) 525, read only memory (ROM) 520, and hybrids thereof.

Storage device 530 may include services 532, 534, and 536 for controlling the processor 510. Other hardware or software modules are contemplated. Storage device 530 may be connected to system bus 505. In one aspect, a hardware module that performs a particular function may include the software component stored in a computer-readable medium in connection with the necessary hardware components, such as processor 510, bus 505, display 535, and so forth, to carry out the function.

FIG. 5B illustrates a computer system 550 having a chipset architecture. Computer system 550 may be an example of computer hardware, software, and firmware that may be used to implement the disclosed technology. System 550 may include a processor 555, representative of any number of physically and/or logically distinct resources capable of executing software, firmware, and hardware configured to perform identified computations. Processor 555 may communicate with a chipset 560 that may control input to and output from processor 555. In this example, chipset 560 outputs information to output 565, such as a display, and may read and write information to storage device 570, which may include magnetic media, and solid state media, for example Chipset 560 may also read data from and write data to RAM 575. A bridge 580 for interfacing with a variety of user interface components 585 may be provided for interfacing with chipset 560. Such user interface components 585 may include a keyboard, a microphone, touch detection and processing circuitry, a pointing device, such as a mouse, and so on. In general, inputs to system 550 may come from any of a variety of sources, machine generated and/or human generated.

Chipset 560 may also interface with one or more communication interfaces 590 that may have different physical interfaces. Such communication interfaces may include interfaces for wired and wireless local area networks, for broadband wireless networks, as well as personal area networks. Some applications of the methods for generating, displaying, and using the GUI disclosed herein may include receiving ordered datasets over the physical interface or be generated by the machine itself by processor 555 analyzing data stored in storage 570 or 575. Further, the machine may receive inputs from a user through user interface components 585 and execute appropriate functions, such as browsing functions by interpreting these inputs using processor 555.

It may be appreciated that example systems 500 and 550 may have more than one processor 510 or be part of a group or cluster of computing devices networked together to provide greater processing capability.

While the foregoing is directed to embodiments described herein, other and further embodiments may be devised without departing from the basic scope thereof. For example, aspects of the present disclosure may be implemented in hardware or software or a combination of hardware and software. One embodiment described herein may be implemented as a program product for use with a computer system. The program(s) of the program product define functions of the embodiments (including the methods described herein) and can be contained on a variety of computer-readable storage media. Illustrative computer-readable storage media include, but are not limited to: (i) non-writable storage media (e.g., read-only memory (ROM) devices within a computer, such as CD-ROM disks readably by a CD-ROM drive, flash memory, ROM chips, or any type of solid-state non-volatile memory) on which information is permanently stored; and (ii) writable storage media (e.g., floppy disks within a diskette drive or hard-disk drive or any type of solid state random-access memory) on which alterable information is stored. Such computer-readable storage media, when carrying computer-readable instructions that direct the functions of the disclosed embodiments, are embodiments of the present disclosure.

It will be appreciated to those skilled in the art that the preceding examples are exemplary and not limiting. It is intended that all permutations, enhancements, equivalents, and improvements thereto are apparent to those skilled in the art upon a reading of the specification and a study of the drawings are included within the true spirit and scope of the present disclosure. It is therefore intended that the following appended claims include all such modifications, permutations, and equivalents as fall within the true spirit and scope of these teachings.

What is claimed is:

1. A method for generating a voxel-based quadratic penalty model for automatic intensity modulated radiation therapy (IMRT) treatment planning, comprising:
    generating, by a computing system, an initial assignment of threshold values to a penalty function of the voxel-based quadratic penalty model for IMRT treatment planning;
    receiving, by the computing system, an update to a dose value associated with the IMRT treatment planning;
    dynamically updating, by the computing system, the threshold values based on the update to the dose value;
    continuing, by the computing system, to iterate the threshold values based on further updates to the dose value; and
    conducting, by the computing system, automatic intensity modulated radiation therapy based on the voxel-based quadratic penalty model and the iterated threshold values.

2. The method of claim 1, wherein the threshold values are initially representative of idealized planning target volume coverage.

3. The method of claim 2, wherein continuing, by the computing system, to iterate the threshold values based on the further updates to the dose value comprises:
    relaxing the threshold values from the idealized planning target volume coverage to a reference dose volume histogram.

4. The method of claim 1, wherein the penalty function comprises a primary penalty and a secondary penalty.

5. The method of claim 4, wherein the primary penalty pulls the dose value toward a reference dose volume histogram by penalizing dose deviations from the threshold values.

6. The method of claim 4, wherein the secondary penalty pulls the dose value towards an ideal value.

7. The method of claim 6, wherein the ideal value is a prescription dose.

8. A system for generating a voxel-based quadratic penalty model for automatic intensity modulated radiation therapy (IMRT) treatment planning, comprising:
    a processor; and
    a memory having programming instructions stored thereon, which, when executed by the processor, performs operations, comprising:
        generating an initial assignment of threshold values to a penalty function of the voxel-based quadratic penalty model for IMRT treatment planning;
        receiving an update to a dose value associated with the IMRT treatment planning;
        dynamically updating the threshold values based on the update to the dose value;
        continuing to iterate the threshold values based on further updates to the dose value; and
        conducting automatic intensity modulated radiation therapy based on the voxel-based quadratic penalty model and the iterated threshold values.

9. The system of claim 8, wherein the threshold values are initially representative of idealized planning target volume coverage.

10. The system of claim 9, wherein continuing to iterate the threshold values based on the further updates to the dose value comprises:
    relaxing the threshold values from the idealized planning target volume coverage to a reference dose volume histogram.

11. The system of claim 8, wherein the penalty function comprises a primary penalty and a secondary penalty.

12. The system of claim 11, wherein the primary penalty pulls the dose value toward a reference dose volume histogram by penalizing dose deviations from the threshold values.

13. The system of claim 11, wherein the secondary penalty pulls the dose value towards an ideal value.

14. The system of claim 13, wherein the ideal value is a prescription dose.

15. A non-transitory computer readable medium having instructions stored thereon, which, when executed by a processor, cause the processor to perform operations, comprising:
- generating, by a computing system, an initial assignment of threshold values to a penalty function of a voxel-based quadratic penalty model for IMRT treatment planning;
- receiving, by the computing system, an update to a dose value associated with the IMRT treatment planning;
- dynamically updating, by the computing system, the threshold values based on the update to the dose value;
- continuing, by the computing system, to iterate the threshold values based on further updates to the dose value; and
- conducting, by the computing system, automatic intensity modulated radiation therapy based on the voxel-based quadratic penalty model and the iterated threshold values.

16. The non-transitory computer readable medium of claim 15, wherein the threshold values are initially representative of idealized planning target volume coverage.

17. The non-transitory computer readable medium of claim 16, wherein continuing, by the computing system, to iterate the threshold values based on the further updates to the dose value comprises:
- relaxing the threshold values from the idealized planning target volume coverage to a reference dose volume histogram.

18. The non-transitory computer readable medium of claim 15, wherein the penalty function comprises a primary penalty and a secondary penalty.

19. The non-transitory computer readable medium of claim 18, wherein the primary penalty pulls the dose value toward a reference dose volume histogram by penalizing dose deviations from the threshold values.

20. The non-transitory computer readable medium of claim 18, wherein the secondary penalty pulls the dose value towards an ideal value.

* * * * *